United States Patent [19]
Chikami

[11] Patent Number: 5,586,881
[45] Date of Patent: Dec. 24, 1996

[54] INDICATOR FOR USE IN FIXING A DEVICE FOR CORRECTING TEETH IRREGULARITIES TO A SURFACE OF EACH TOOTH

[75] Inventor: Kunio Chikami, 211-1, Minamikuma, Kochi-shi, Kochi-ken, Japan

[73] Assignee: Kunio Chikami, Kochi, Japan

[21] Appl. No.: 345,418

[22] Filed: Nov. 21, 1994

[30] Foreign Application Priority Data

Jul. 25, 1994 [JP] Japan ..................................... 6-172190

[51] Int. Cl.$^6$ ....................................................... A61C 3/00
[52] U.S. Cl. ................................................................ 433/3
[58] Field of Search ..................................................... 433/3

[56] References Cited

U.S. PATENT DOCUMENTS

| | | | |
|---|---|---|---|
| 4,035,919 | 7/1977 | Cusato | 433/3 |
| 4,455,137 | 6/1984 | Diamond | 433/3 |
| 4,626,208 | 12/1986 | Hall | 433/3 |
| 4,850,864 | 7/1989 | Diamond | 433/3 |

Primary Examiner—John J. Wilson
Attorney, Agent, or Firm—Armstrong, Westerman, Hattori, McLeland & Naughton

[57] ABSTRACT

An indicator for using in setting a device for teeth irregularities including a wire extending along with a dentition, a bracket in which the wire is inserted, the bracket being fixed to a surface of each tooth in a manner that a pillow-like shaped base plate is interposed between the bracket and the surface, the indicator including: a backbone member extending along with a longitudinal axis in the tooth; a leg member connected with a lower end of the backbone member; a first arm member connected with an upper end of the backbone member, the first arm member extending parallel to the leg member; a device for carrying the bracket for slidably carrying in a slidable manner, the device being connected with the backbone member at intermediate portion of the backbone member; and at least one second arm member connected with the backbone member at intermediate portion between a position where the means is connected and another position where the leg member is connected the second arm member extruding parallel to the leg member.

5 Claims, 13 Drawing Sheets

INDICATOR FOR USE IN FIXING A DEVICE FOR CORRECTING TEETH IRREGULARITIES TO A SURFACE OF EACH TOOTH

BACKGROUND OF THE INVENTION

The present invention relates to an indicator for use in fixing a device for correcting teeth irregularities to a surface of each tooth. More particularly, the present invention relates to the indicator for use in fixing the device for correcting teeth irregularities to a surface of each tooth in order to correct a distorted tooth to have a desired posture, and to keep the desired posture.

As shown in FIGS. 12 and 13, in order to correct teeth irregularities including a tooth Ta having an abnormal posture such as a distortion, and to shift to a normal state and keep the state, a device for correcting teeth irregularities (hereinafter referred to as a device) comprising a bracket 8 and a wire 14 which is inserted into the bracket 8 has hitherto been fixed to the surface of the tooth in a manner that a base plate 9 is interposed between the bracket 8 and the surface whereby orthodontic treatment is performed (with reference to Japanese Unexamined Patent Publication No. 212345/1992).

As another orthodontic treatment, brackets having a desired posture corresponding to each tooth are prepared, whereby orthodontic treatment is performed by adhering each of said brackets directly to the surface of the tooth with adhesive.

With respect to the orthodontic treatment shown in FIGS. 12 and 13, dentists are required to press the bracket, which is provided with a pillow-like shaped base plate adhered with adhesive beforehand, against the surface of the tooth. Further, the dentists are required to decide a desired position to be set and a desired posture by pinching the bracket with a thumb and a finger depending on their experience and flair.

However experienced the dentists may be, it is difficult to accurately decide the desired position to be set and the desired posture of the bracket.

On the other hand, with respect to the other orthodontic treatment in which the bracket is directly fixed to the surface of the tooth adhered with adhesive, the bracket can be easily fixed to the surface to the tooth if only the position to be fixed is decided since the posture is decided beforehand. However, with respect to this orthodontic treatment, it is difficult to finish the surface of the bracket in such a manner as to conform with the surface of the tooth having a complex shape. For that reason, a surface of the bracket coming into contact with the surface of the tooth is conformed with the surface of the tooth. Further, the base plates should be prepared having a different shape depending on the shape of each tooth. For that reason, there is a problem in which the number of parts constituting the bracket is increased.

The object of the present invention is to provide an indicator used to decide both the position to fix the bracket to the surface of the tooth and the posture, said indicator being used for setting the device for correcting the teeth irregularity in which the base plate is interposed between the bracket and the surface of each tooth.

SUMMARY OF THE INVENTION

An indicator of the present invention used for setting a device for correcting teeth irregularities consisting of a wire extending along with the tooth and a bracket into which said wire is inserted, said bracket being fixed to a surface of said tooth in a manner that a pillow-like shaped base plate is interposed between said bracket and said surface; said indicator comprising:

a backbone member extending along a longitudinal axis of said tooth;

a leg member, one end of which is connected with a lower end of said backbone member;

a first arm member, one end of which is connected with an upper end of said backbone member, said first member extending parallel to said leg member;

a means for carrying said bracket, in a slidable manner, said means being positioned at an intermediate, part of said backbone member;

at least one second arm member, one end of which is positioned at an intermediate part between a place where said means is connected and another place where said leg member is connected to said backbone member.

The indicator of the present invention allows the bracket to fix to the surface of each of said tooth at a predetermined position of each of said tooth without depending on experience and flair of dentists while keeping a desired posture of each tooth.

DETAILED DESCRIPTION

The indicator of the present invention will be described in detail with reference to attached Figures.

Figure 1:
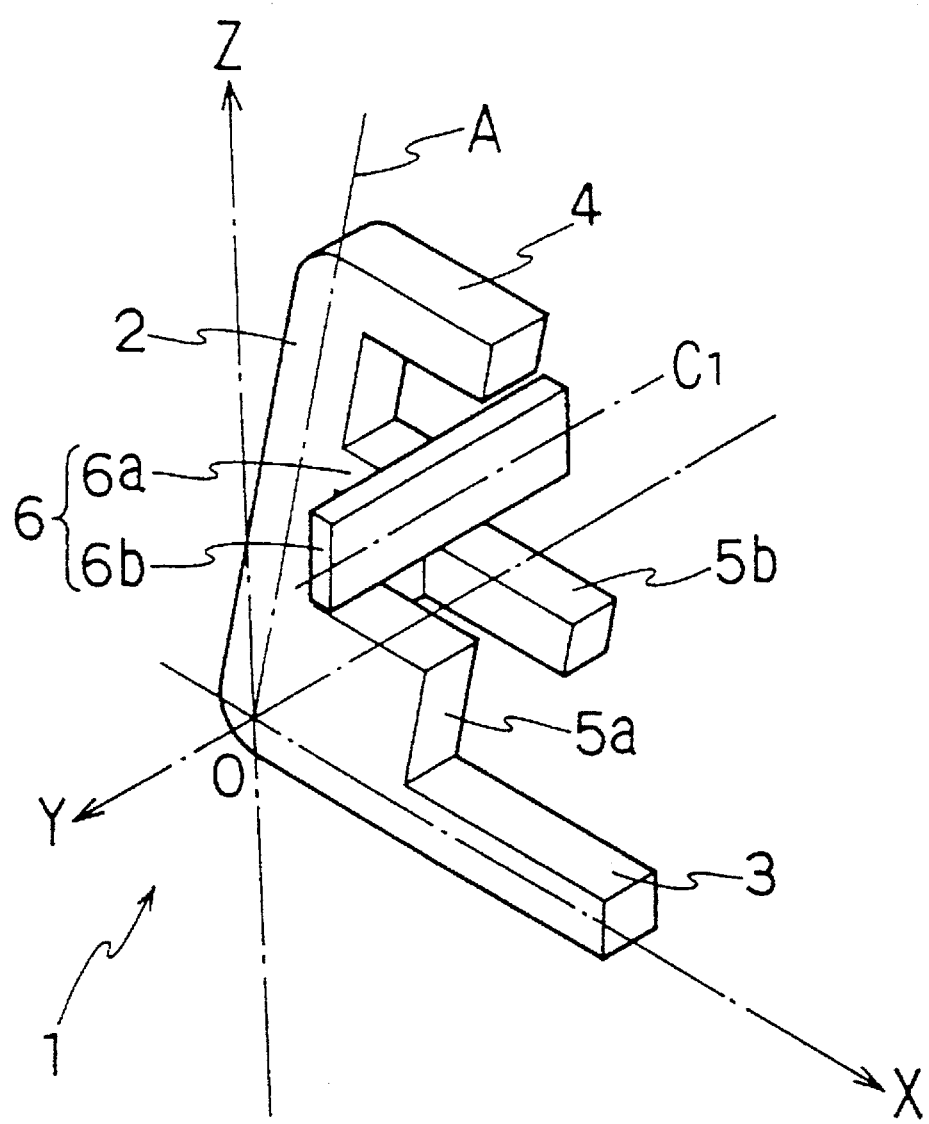
FIG. 1 is a perspective view showing an embodiment of the indicator of the present invention.

FIG. 1 is a perspective view showing an embodiment of the indicator of the present oriented with respect to an OX axis, OY axis and OZ axis.

The indicator 1 comprises a backbone member 2, a leg member 3, a first arm member 4, a second arm member 5 and a means for carrying a bracket. The means for carrying a bracket comprises a support member 6a and a rectangular plate 6b for coming into contact with a bracket (not shown in FIG. 1), said plate 6b being fixed to the support member 6a.

Figure 2A:
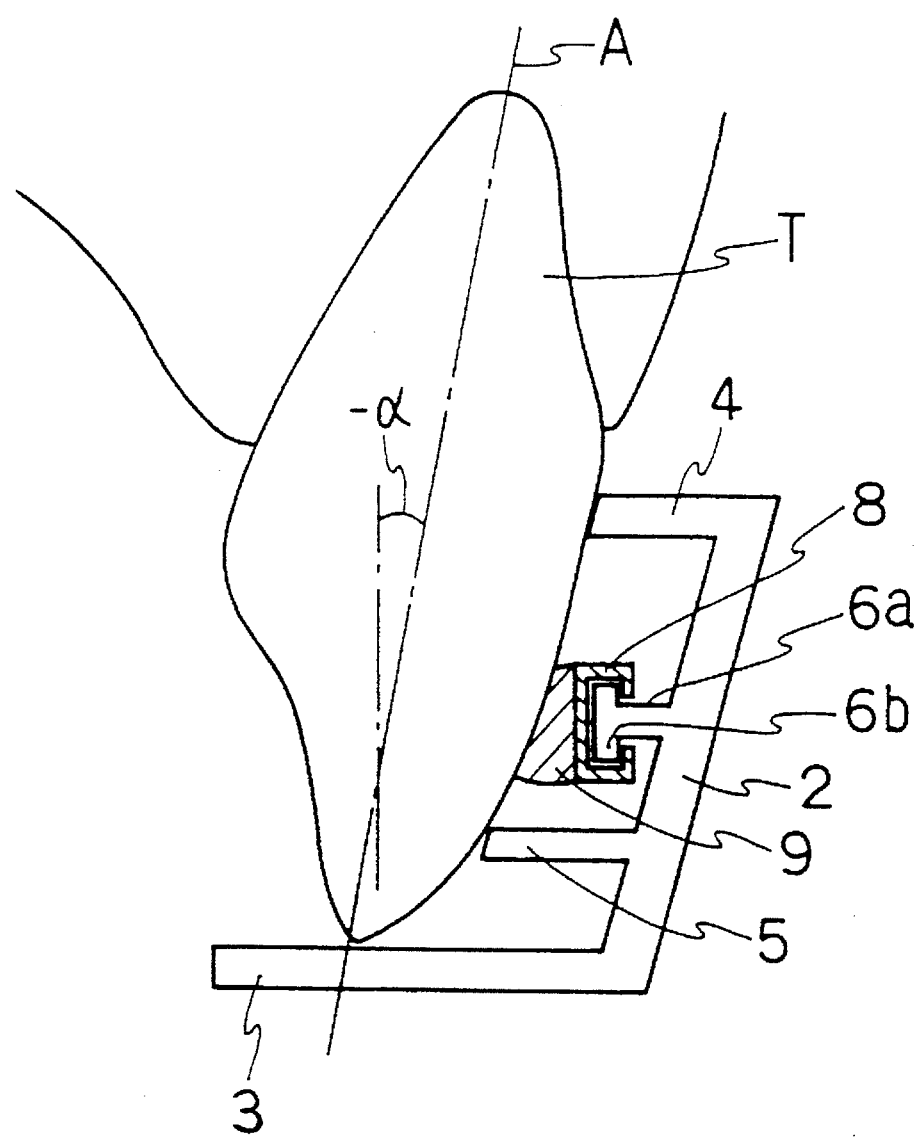
FIGS. 2(*a*) and 2(*b*) are side views showing a state in which the bracket is fixed to the surface of the tooth using the indicator of FIG. 1.
Figure 2B:
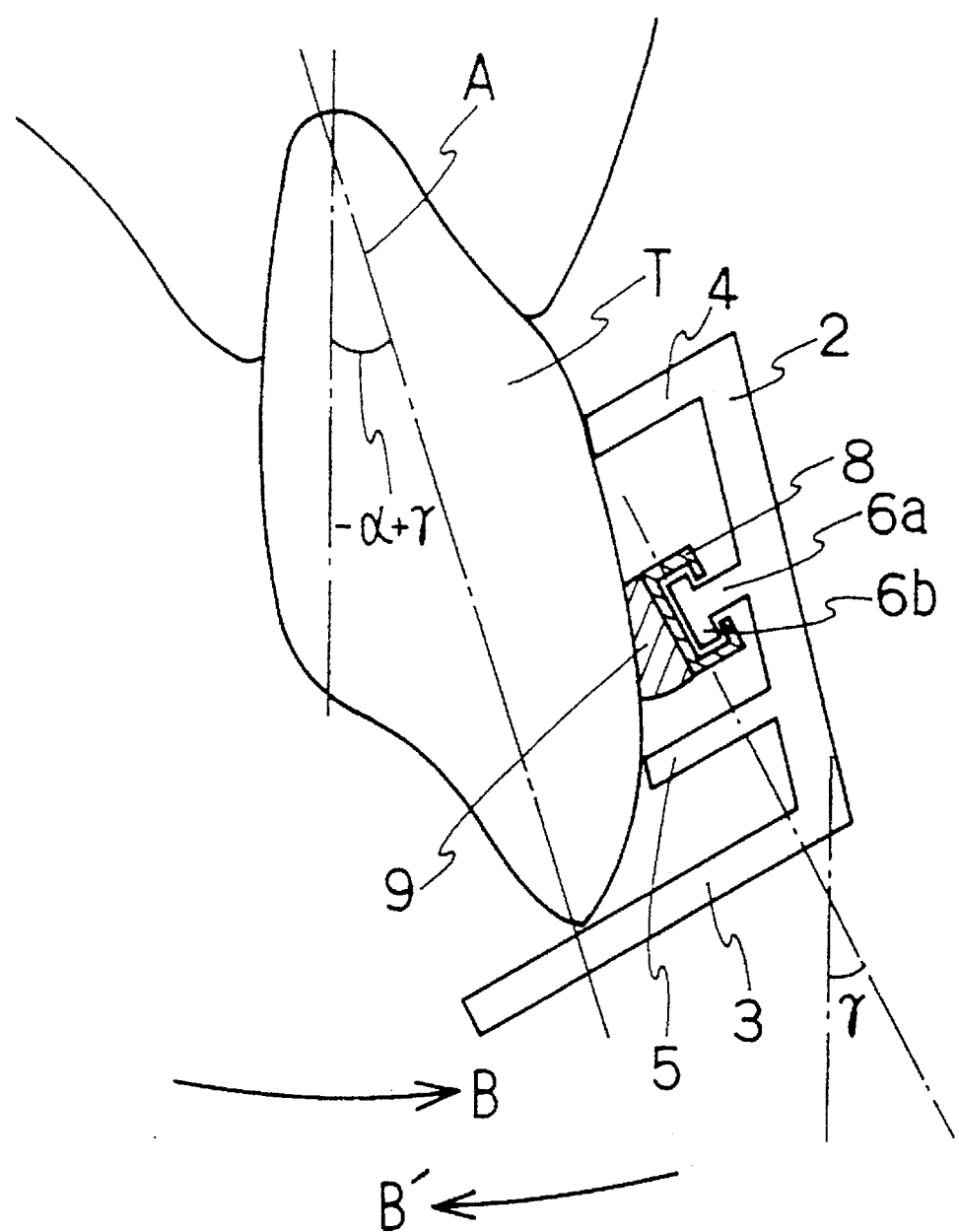
Figure 3A:
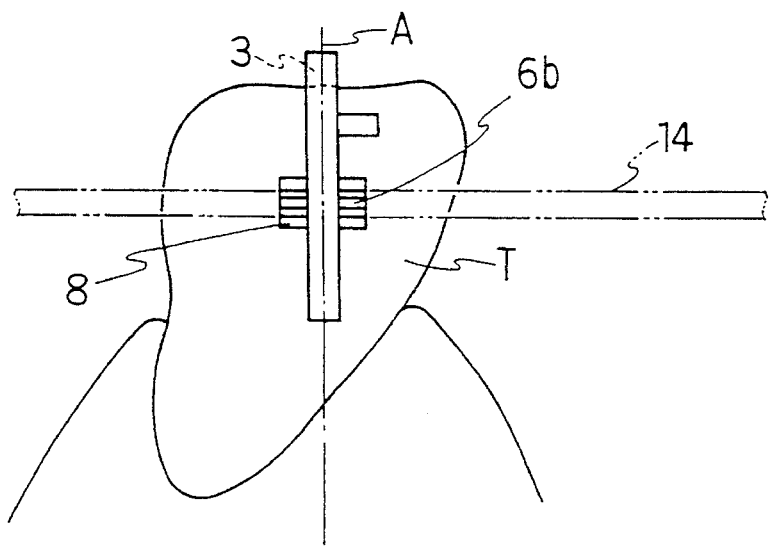
FIGS. 3(*a*) and 3(*b*) are front views showing a state in which the bracket is fixed to the surface of the tooth using another embodiment of the indicator of the present invention.
Figure 4A:
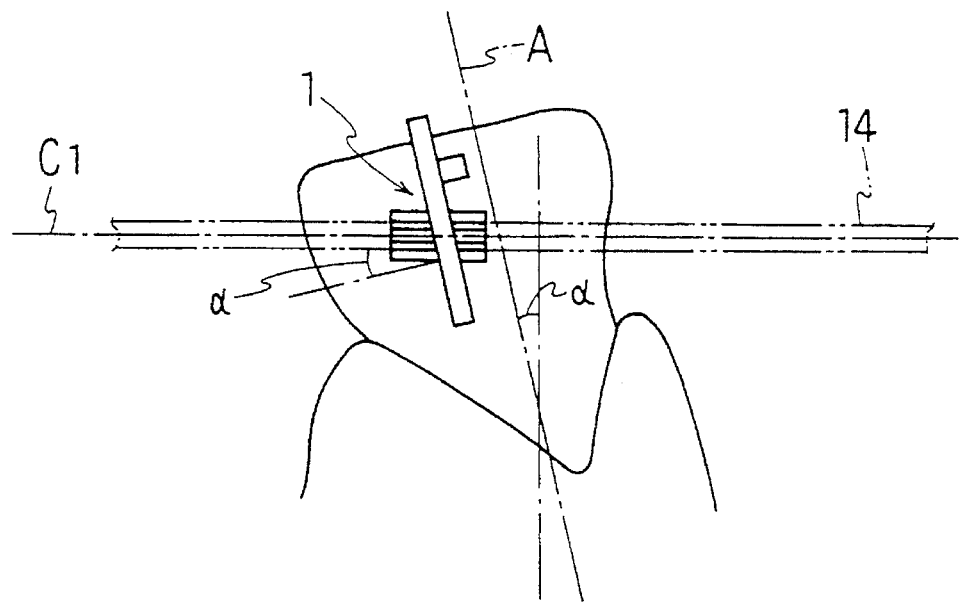
FIGS. 4(*a*) and 4(*b*) are front views showing a state in which the bracket is fixed to the surface of the tooth using still another embodiment of the indicator of the present invention.
Figure 4B:
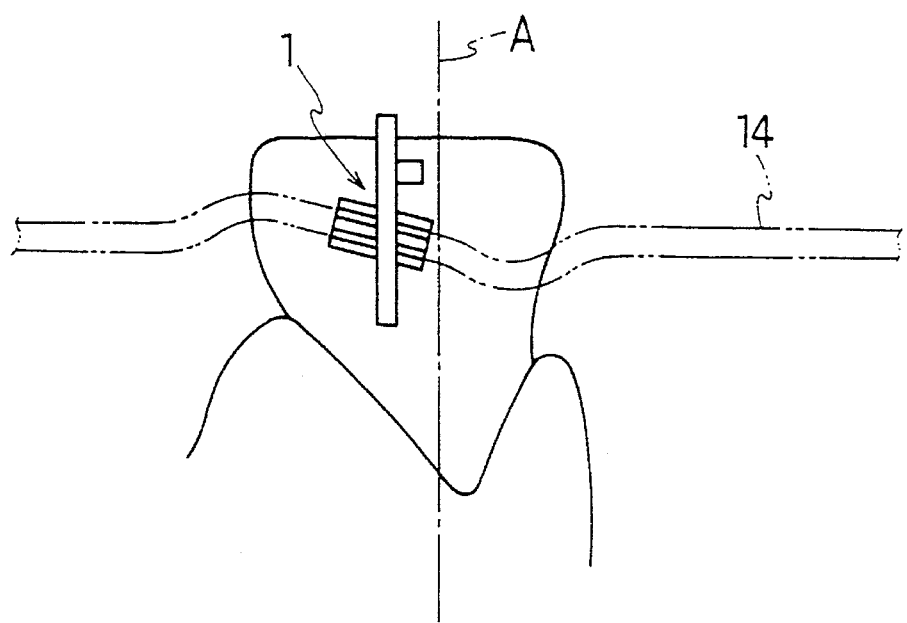
Figure 5A:
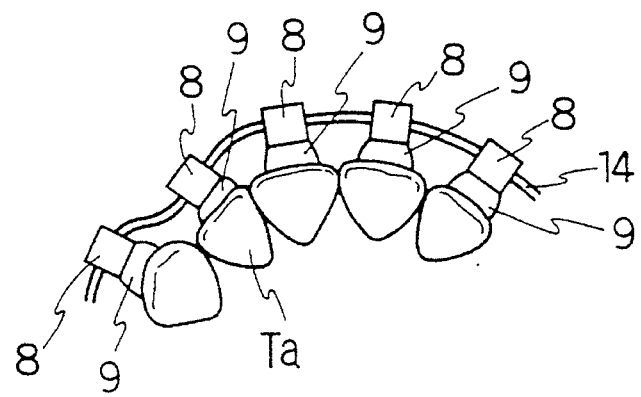
FIGS. 5(*a*), 5(*b*) and 5(*c*) are plan views showing a state in which the bracket is fixed to the surface of the tooth using yet another embodiment of the indicator of the present invention.
Figure 5B:
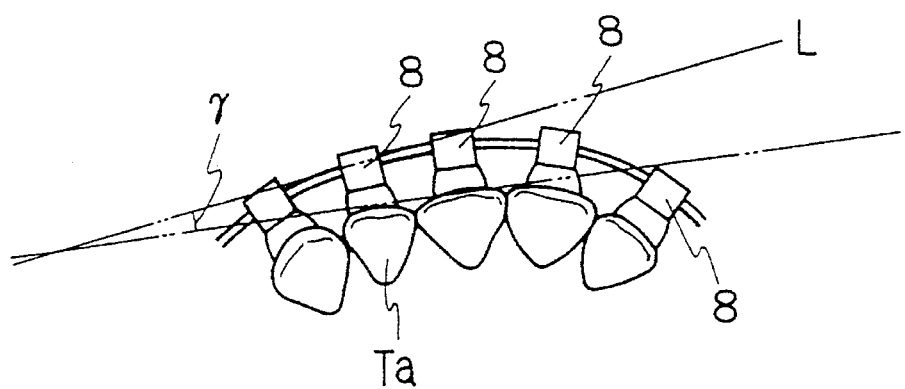

As shown in FIG. 2(a), FIG. 3(a) and FIG. 5(b), each tooth is somewhat twisted about an OX axis, an OY axis and an OZ axis in a normal state of the tooth. In teeth of mankind, each of angles (theorical value) of twisted about the OX axis, OY axis and OZ axis respectively are substantially the same value though there is a deviation among different raws. For that reason, by virtue of the indicator of the present invention, the position for setting the bracket to the surface of the tooth and the posture of the bracket can be obtained if each size of elements constituting the indicator 1 is decided by measuring: ① a distance from a tip of the tooth; and ② each of the twisted angles about the OX axis, the OY axis and OZ axis using a model of correct dentition. A method for setting the bracket on the surface of the tooth by using thus obtained indicator will be explained with reference to FIGS. 2 to 5.

The tooth T shown in FIG. 2(a) is a cross sectional view of the tooth having a correct posture in a specific region of a dentition. In case of the tooth, the longitudinal axis of the tooth extended to the direction inclining ($-\alpha$) toward the OZ axis in the rectangular coordinates. The state is normal posture.

The tooth T shown in FIG. 2(b) is another tooth which is positioned at the same region in the dentition as the tooth shown in FIG. 2(a). This tooth is abnormally twisted around the OY axis (twisted in the direction of arrow B) in the rectangular coordinate shown in FIG. 11.

Firstly, the bracket 8 is set to the rectangular plate 6b of the indicator 1. A suitable amount of adhesive agent is applied to a surface opposed to the surface of the tooth, thereafter base material for a base plate 9 is pressed against the surface to which the adhesive agent is applied. In order to fix the base plate 9 to the surface of the tooth, suitable adhesive agent is applied to a surface of the base material.

Next, while the backbone member 2 is kept parallel to the surface of the tooth T, that is parallel to the longitudinal axis A, the indicator 1 is moved while contacting the leg member 3 with a tip of the tooth T, thereby the position for setting bracket, that is a distance from the tip of the tooth is decided. As a result, each free end of the first arm member 4 and the second arm member 5 is contacted with the surface of the tooth, so that the base plate can be suitably fixed to the surface of the tooth.

In turn, the base material is cured by exposing to a light beam so that the base plate 9 is obtained. Thereafter, the indicator 1 is separated from the bracket 8 while moving the bracket 8 along with the OY axis. Please note that the base material can be cured by exposing to a light beam after separating from the indicator 1, so that the base plate 8 can be obtained. Setting the indicator 1 to the surface of the tooth is performed in the above method whether the tooth has a correct posture or not.

After the bracket 8 is fixed to the surface of each of the teeth including a tooth having irregular posture as shown in FIG. 2(b), a wire 14 is inserted into each of brackets 8. In case of the tooth having a correct posture, the bracket 8 is fixed to the surface of the tooth as shown in FIG. 2(a). Whereas in case of the tooth shown in FIG. 2(b), the longitudinal axis A of said tooth is inclined at ($-\alpha+\gamma$) toward the vertical axis. For that reason, a region of the wire 14, said region corresponding to said tooth is twisted at $\gamma$ toward the vertical axis.

A turning effect in the direction of arrow B' due to restoring force of said region of the wire 14 is applied to the tooth shown in FIG. 2(b), so that the tooth is corrected to have a desired posture. Said turning effect is called a torque.

Figure 3B:
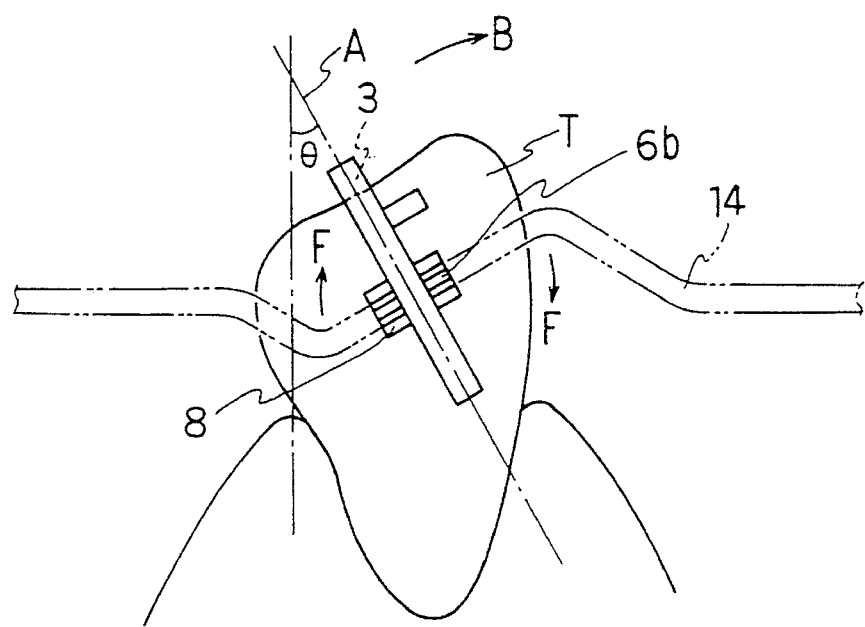
Figure 11A:
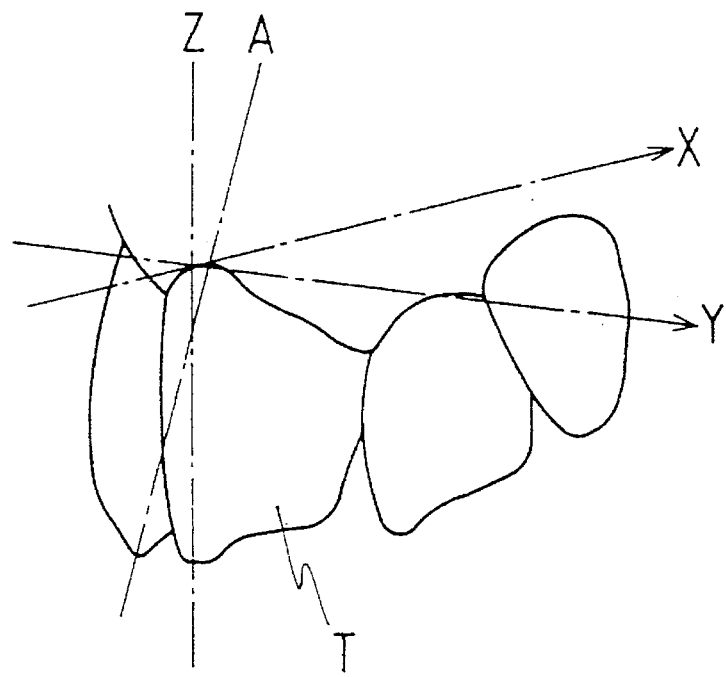
FIGS. 11(*a*) and 11(*b*) are explanatory views showing a positioned relation of the teeth in rectangular coordinates defined by an OX axis, an OY axis and an OZ axis.
Figure 11B:
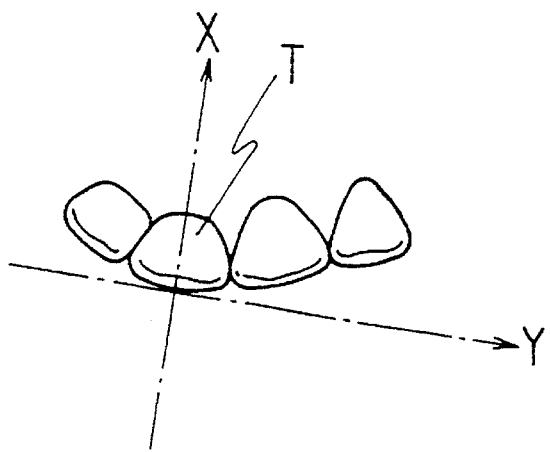
Figure 12:
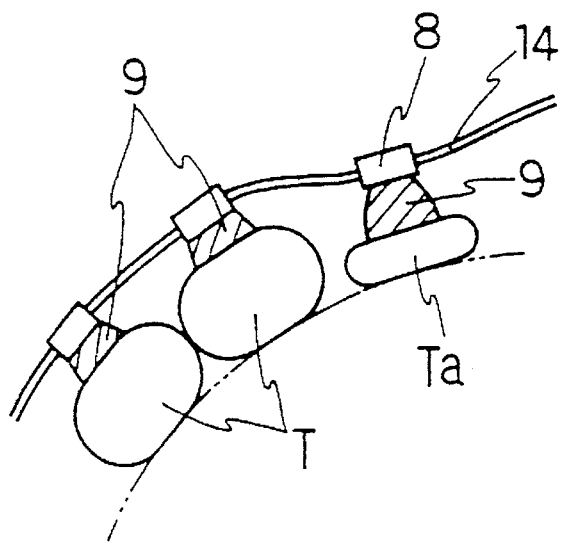
FIG. 12 is an explanatory view showing a state in which the device for correcting teeth irregularities is fixed to the surface of the tooth to be corrected in a manner that the base plate is interposed between the surface of the tooth and the bracket.
Figure 13:
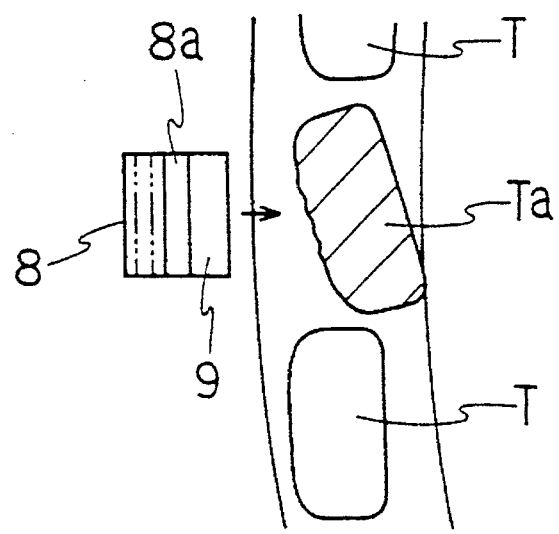
FIG. 13 is a schematic plan view showing an example of a method for setting the device for correcting the teeth irregularities to the tooth.

FIG. 3(b) shows a case in which the orthodontic treatment is performed by applying another turning effect about the OY axis in the rectangular coordinates shown in FIG. 11 to the tooth. In case of the tooth having a posture shown in FIG. 3(a) and FIG. 3(b), the tooth shown in FIG. 3(a) has a correct posture. The method for fixing a bracket to the surface of the tooth is substantially the same as the method for the tooth shown in FIG. 2(a) and FIG. 2(b). That is, while the leg member 3 is contacted with a tip of the tooth while keeping the backbone member parallel to the longitudinal axis A of the tooth, the bracket 8 is fixed to the surface of the tooth in a manner that the base plate (not shown) is interposed between the bracket into which the wire is inserted and the tooth. Thereafter, the base plate is cured by exposing to the light beam. Then, the indicator 1 is separated from the bracket 8. Please note that after separating the indicator 1 from the bracket 8, the base plate can be cured by exposing to the light beam. After the bracket 8 is fixed to the surface of the tooth as shown in FIG. 3, the wire 14 is inserted into the bracket. At this time, the wire 14 is distorted as shown in FIG. 3(b) so that force F is generated from the wire 14 due to the restoring force of the wire 14. For that reason, the tooth T is corrected by another turning effect in the direction of arrow 13. Said another turning effect is called an angulation.

FIG. 4 shows a case of correcting method of correcting the tooth in which the longitudinal axis of the tooth is extended in the direction inclining at A toward the vertical axis in the normal posture. The principle of correcting the irregular posture is substantially the same as the tooth shown in FIG. 3 except that a transverse axis C1 of the rectangular plate 6b is inclined at ($\alpha$). In the tooth having a correct posture (with reference to FIG. 4(a)), the wire 14 is not distorted, while in the irregular posture, the angulation is applied to the tooth though the wire 14 is distorted.

Figure 5C:
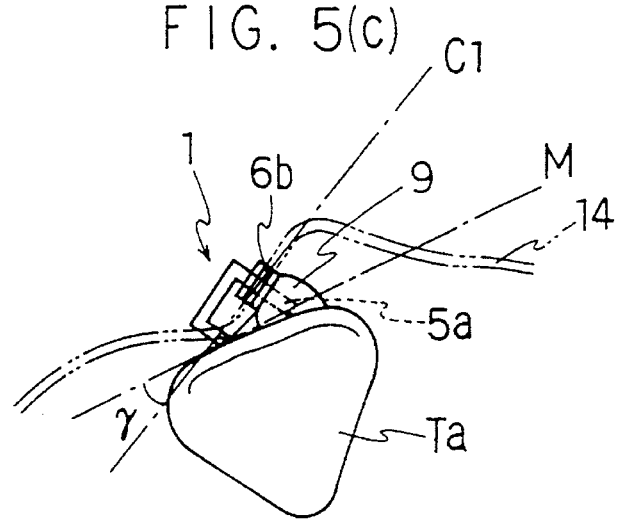
Figure 6:
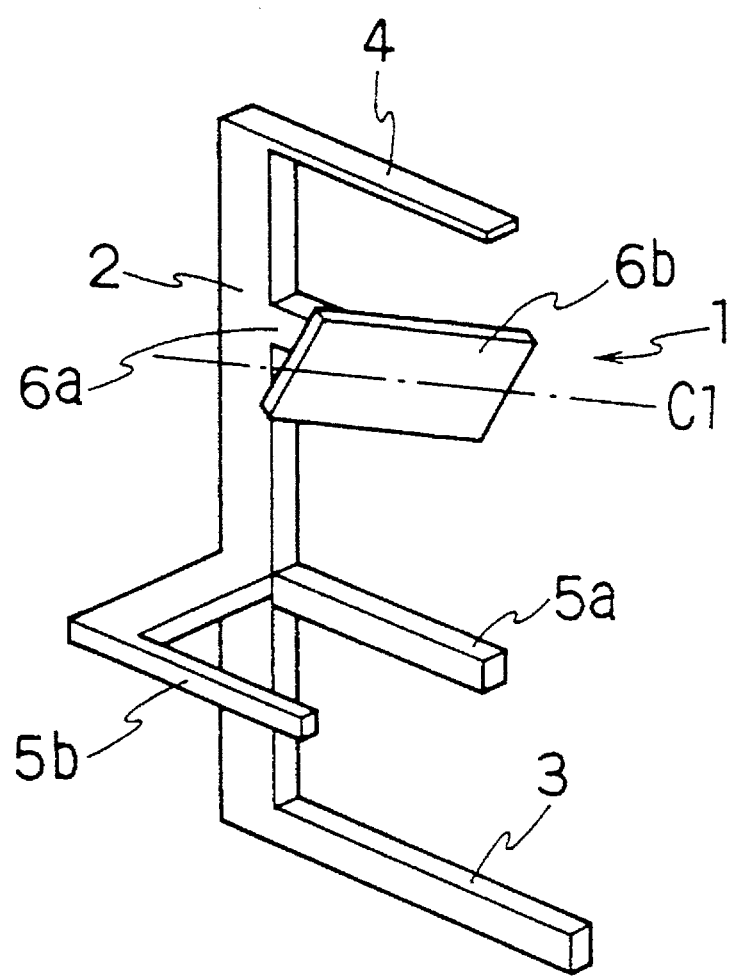
FIG. 6 is a perspective view showing yet another embodiment of the indicator of the present invention.
Figure 10:
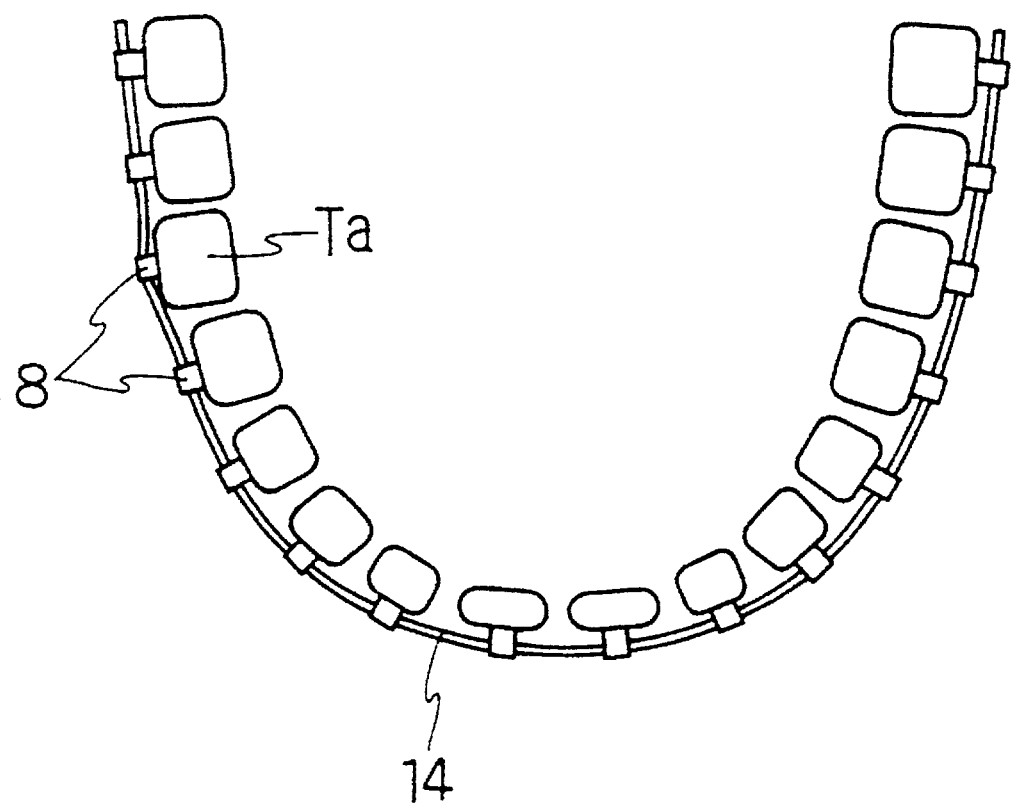
FIG. 10 is a plan view illustrating a state in which the device for correcting teeth irregularities is fixed to each of the teeth including a tooth to be corrected.

FIG. 5(a), FIG. 5(b) and FIG. 5(c) are plan views partially showing a dentition. FIG. 5(a) shows a dentition including the tooth Ta to be corrected, whereas FIG. 5(b) shows the tooth having a desired posture after orthontic treatment. FIG. 5(c) is a plan view showing a main part of FIG. 5(a). In case of the tooth Ta, such a tooth is correct that the surface of the tooth is inclined at $\gamma$ toward a tangent L to the wire 14 (with reference to FIG. 10) having an arch-like shape at the position where the wire is inserted into the bracket (with reference to FIG. 5(b)).

In order to correct the tooth, the indicator 1 of the present invention is arranged such that the indicator has arm members 5a, 5b having different length, a line M passing through each free end of the arms 5a, 5b is inclined at γ toward the transverse line C1 of the rectangular plate 6b (with reference to FIG. 5(c)). When the bracket 8 is fixed to the surface of the tooth by using such indicator 1, and the wire 14 is inserted into the bracket 8, the wire 14 is distorted as shown in FIG. 5(c) so that still another turning effect due to a restoring force of the wire 14 is applied to the tooth Ta to have a desired posture as shown in FIG. 5(b).

Figure 7A:
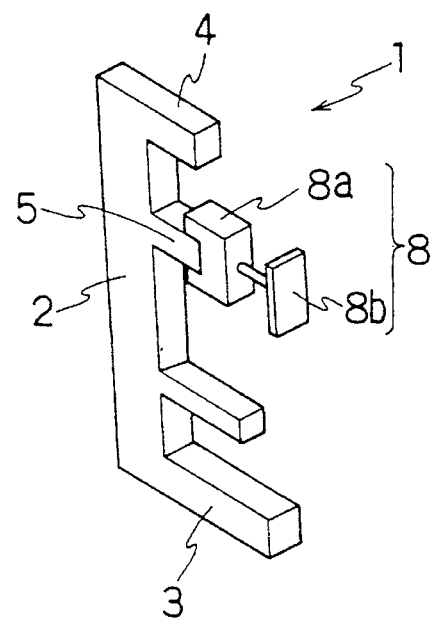
FIGS. 7(*a*) and 7(*b*) are explanatory views showing yet another embodiment of the indicator of the present invention.
Figure 7B:
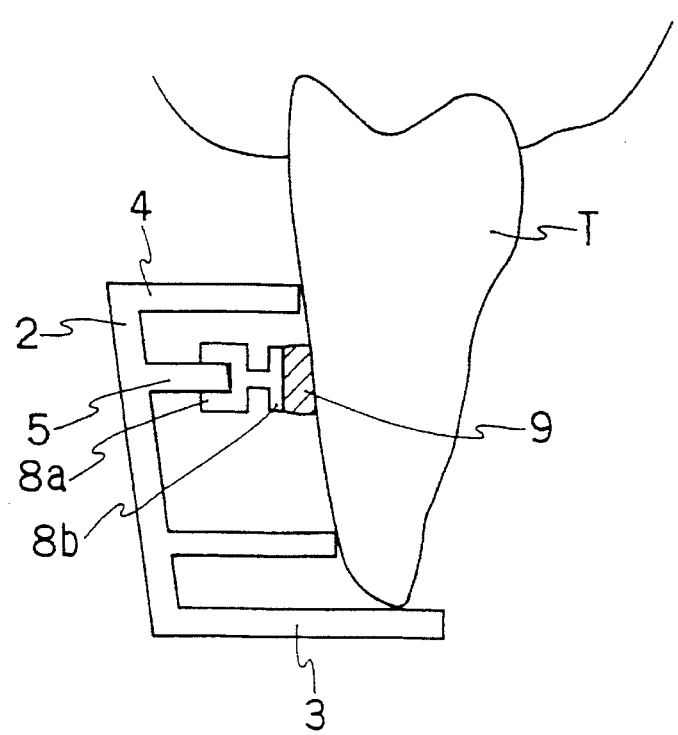
Figure 8:
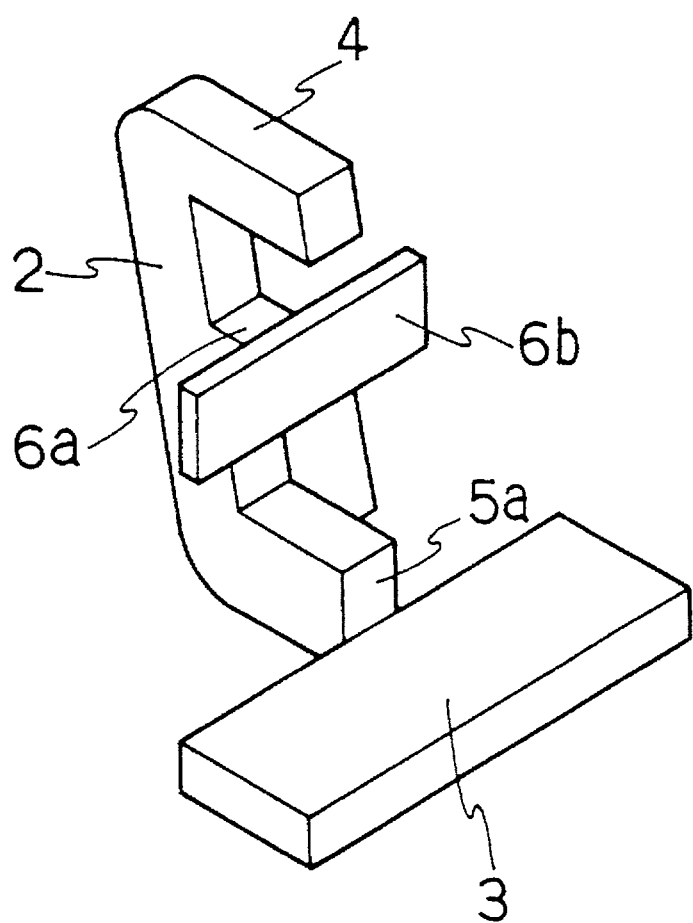
FIG. 8 is a perspective view showing yet another embodiment of the indicator of the present invention.
Figure 9:
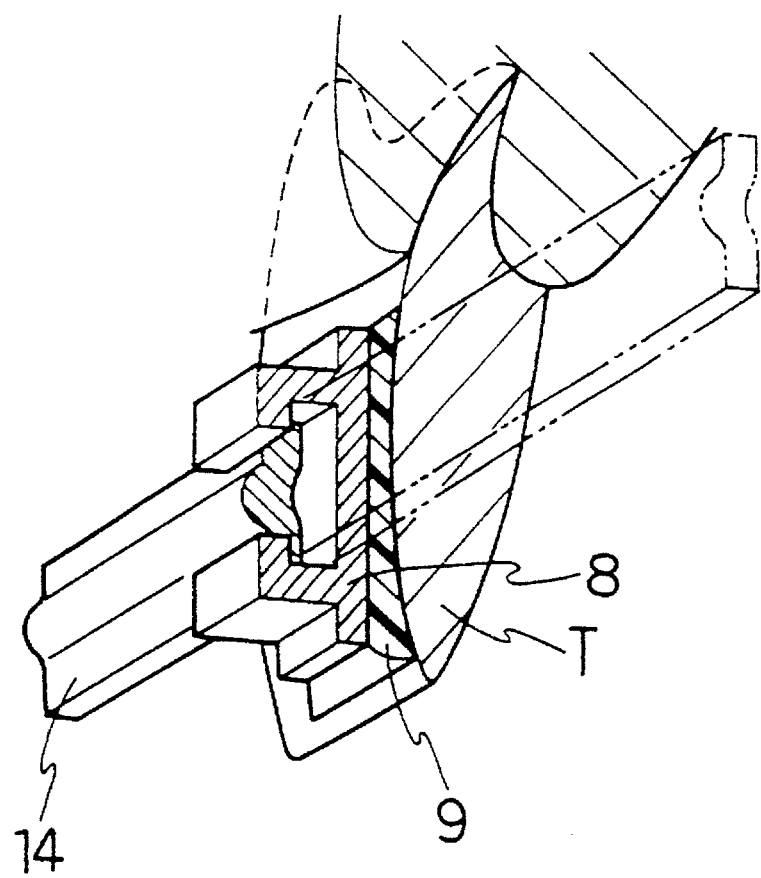
FIG. 9 is a perspective view partly in section showing a main part of the device for correcting teeth irregularities showing a state after the device is set using the indicator of the present invention.

FIGS. 7(a) and 7(b) show the indicator 1 for setting a bracket 8 for a conventional metallic wire. Said bracket 8 comprises a wire support member 8a formed into a tuning-fork-like shape and a base member 8b. Even the bracket 8 can be fixed to the tooth in a manner that the base plate is interposed between the bracket 8 and the tooth by using the indicator 1 of the present invention. Method for using said indicator is substantially the same as that shown in FIGS. 2 to 5.

The base plate is composed of the easily plastically deformable resin. As the easily plastically deformable resin, dental materials e.g. thermosetting resin such as epoxy resin, acrylic resin, phenolic resin, photocurable resin such as epoxy resin, acrylic ultraviolet crosslinking resin, thermosetting resin such as polyolefin resin, polyester resin, polyamide resin, polyimide resin, polycarbonate resin, which are conventionally known, can be employed. The photocurable resin is most preferable.

By the effect of the indicator of the present invention, the bracket can be fixed to the surface of the tooth at the predetermined position while keeping a desired posture by the simple procedure for using the indicator without highly experienced technique to prepare the base plate by understanding the positional relation between the irregular posture and the desired posture and the desired posture of each tooth in a three-dimentional space.

Though several embodiments of the invention are described above, it is to be understood that the present invention is not limited to the above-mentioned embodiments, and various changes and modifications may be made in the invention without departing from the spirit and scope thereof.

What is claimed is:

1. An indicator for using in setting a device for teeth irregularities comprising a wire extending along with a dentition, a bracket in which said wire is inserted, said bracket being fixed to a surface of each tooth in a manner that a pillow-shaped base plate is interposed between said bracket and said surface, said indicator comprising:

a backbone member extending along a longitudinal axis in said tooth;

a leg member connected with a lower end of said backbone member;

a first arm member connected with an upper end of said backbone member, said first arm member extending parallel to said leg member;

a means for carrying said bracket in a slidable manner, said means being connected with said backbone member at an intermediate portion of said backbone member; and at least one second arm member connected with said backbone member at an intermediate portion between a position where said means for carrying said bracket is connected and another position where said leg member is connected, said second arm member extending parallel to said leg member, wherein in a state where the indicator is slidably provided with the bracket that the pillow-shaped base plate is adhered to the bracket, the pillow-shaped base plate is contacted with the tooth and each free end of the first arm member and second arm member contact the tooth.

2. The indicator of claim 1, wherein said means for carrying said bracket comprises a support member connected with said backbone member, said support member extending parallel to said leg member and a rectangular plate member for slidably carrying said bracket in the longitudinal direction which is secured to said support member.

3. The indicator of claim 1, wherein a transverse axis of said rectangular plate is inclined toward a vertical axis.

4. The indicator of claim 2, having two sets of said second arm member having different length.

5. The indicator of claim 2 having two sets of said second arm having same length.

\* \* \* \* \*